March 5, 1974 W. A. WARRINER Plant Pat. 3,510
ROSE PLANT
Filed Sept. 28, 1972
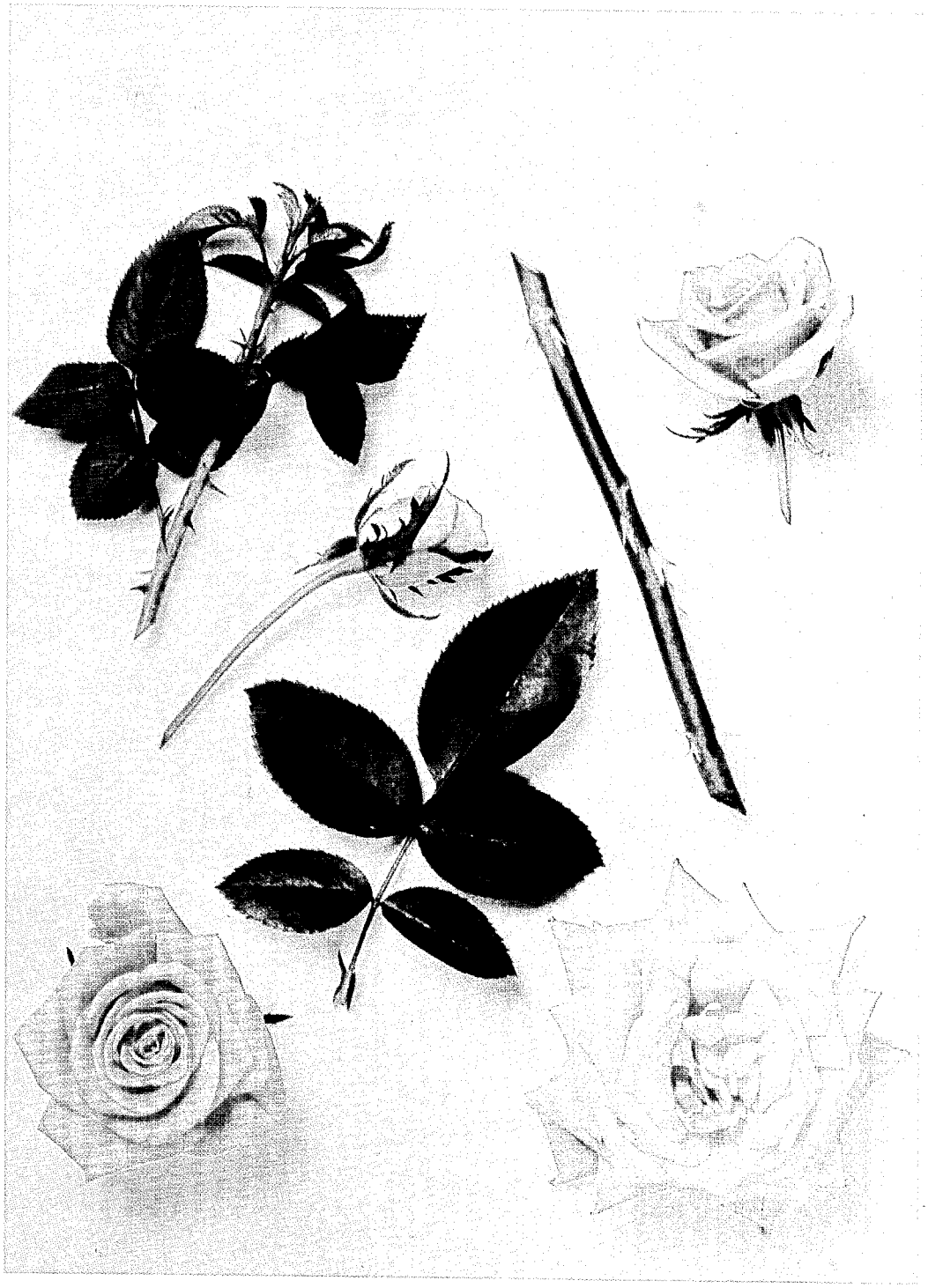

United States Patent Office

Plant Pat. 3,510
Patented Mar. 5, 1974

3,510
ROSE PLANT

William A. Warriner, Tustin, Calif., assignor to Jackson & Perkins Company, Medford, Oreg.

Filed Sept. 28, 1972, Ser. No. 292,892
Int. Cl. A01h 5/00
U.S. Cl. Plt.—17 1 Claim This present invention relates to a new and distinct variety of rose plant in a class intermediate between hybrid tea and floribunda which was originated by me by crossing the variety Tropicana, U.S. Pl. Pat. 1969 with the pollen of the variety Zorina, U.S. Pl. Pat. 2321.

The primary objective of this breeding was to produce a new rose variety comparable to both parents in color, but intermediate between the two in size and plant habit. This objective was substantially achieved along with other desirable improvements as evidenced by the following unique combination of characteristics which are outstanding in the variety of which distinguish it from its parents as well as from all other varieties of which I am aware:

(1) A unique habit of growth, producing long stemmed clusters of flowers on each basal branch.
(2) Much basal branching, thereby developing a rounded, dense plant of about four feet in height in California, similar in habit to the floribunda class but larger in size.
(3) Many flowers produced on secondary or lateral branches without clustering.
(4) Bud color of Signal red opening to Mandarin red.
(5) A high degree of resistance to rose powdery mildew.
(6) Several, up to seven, of upper leaves on each stem having only three leaflets, while most rose varieties have only one or two or no trifoliate leaves.

Asexual reproduction of this new variety by budding, as performed at Wasco, Calif., shows that the foregoing characteristics and distinctions come true to form and are established and transmitted through succeeding propagations.

The accompanying drawing show typical specimens of the vegetative growth and flowers of this new variety in different stages of development, depicted in color as nearly true as it is reasonably possible to make the same in a color illustration of this character.

The following is a detailed description of my new rose variety with color terminology in accordance with Wilson's Horticultural Color Chart, except where ordinary dictionary significance of color is indicated.

Parentage: Seedling
*Seed parent.*—Tropicana U.S.P.P. 1969.
*Pollen parent.*—Zorina U.S.P.P. 2,321.
Classification:
*Botanic.*—*Rosa hybrid.*
*Commercial.*—Between hybrid tea and floribunda.

FLOWER

Observations were made at Irvine, Calif. in August, in the afternoon, of garden and greenhouse specimens.

Blooming habit: Recurrent—continuous.
Bud:
*Size.*—¾ inch to 1 inch when petals start to unfurl.
*Form.*—Blunt top.
*Color.*—When sepals first divide near Signal red (719) in garden and greenhouse. When half blown; inside of petals (garden) Mandarin red (17/1) shaded on outer areas of petals with a color more intense but of same hue as Signal red (719). (Greenhouse) uniformly Mandarin red (17/1). Reverse of petals same.
*Sepals.*—Color: Outer surface—Scheeles green (860/3), overlaid in irregular areas with Scheeles green (860). Inner surface—Lightly tomentose, mostly same color as outer surface. Three appendaged sepals heavily appendaged. Two unappendaged sepals smooth edged.
*Receptacle.*—Color: Scheeles green (860/3). Shape: Conical. Size: Small and slender. Surface: Slightly glandular.
*Peduncle.*—Length: Short. Surface: Slightly glandular. Color: Light green. Strength: Stiff and erect.
*Opening.*—Spiral fashion, petals curl slightly.

Bloom:
*Size.*—Medium. Average size when fully expanded, 3 inches to 3½ inches.
*Borne.*—Singly and in rounded clusters on garden plants, clusters have long stems—8 to 14 inches.
*Stems.*—Long and strong.
*Form.*—When first open, high center. Permanence—outer petal edges slightly curled.
*Petalage.*—Number of petals under normal conditions about 30.
*Color.*—Center of flower: Upper side of petals: (Garden) slightly darker than Azalea pink (618). (Greenhouse) Very close to Azalea pink (618). Reverse side of petals same. Outer petals: Upper side of petals: (Garden) darker than Azalea pink (618) shaded on outer edges to Signal red (719). (Greenhouse) same as center of flower. Reverse side of petals same. Base of petals (garden and greenhouse) small area of Straw yellow (604/2). General tonality from a distance: (Garden) Azalea pink (618) shaded on outer petals with Signal red (719). (Greenhouse) Azalea pink.
*Discoloration.*—No discoloration at end of first day. By third day fades very little.
*Fragrance.*—Slight.

Petals:
*Texture.*—Thick.
*Surface.*—Inside—satiny. Reverse—satiny.
*Shape.*—Round.
*Form.*—Edges slightly quilled.
*Arrangement.*—Irregular.
*Petaloids in center.*—Few, large.
*Persistence.*—Drop off cleanly.
*Lastingness.*—On the plant—long. As cut flower—long.

Reproductive parts:
*Stamens, anthers.*—Medium, many. Color—yellow ochre (07). Arrangement—regular around styles.
*Stamens, filaments (threads).*—Medium. Color—reddish.
*Pollen.*—Golden yellow.
*Styles.*—Loosely separated, of uneven lengths, long.
*Stigmas.*—Color—near Egyptian buff (407/3).
*Ovaries.*—All enclosed in calyx.

PLANT

Form: Bush.
Growth: Very vigorous, upright, branching.
Foliage: Number of leaflets on normal midstem leaves, 5.
*Size.*—Medium.
*Quantity.*—Abundant.
*Color.*—New foliage: (Garden) near Garnet brown (00918/1). (Greenhouse) lighter than Garnet brown (00918/3) on edges. Near Scheeles green (860/3) center of leaflet. Old foliage: (Garden and greenhouse) near Spinach green (0961/1) on upper side, near Lavender green (000761) on lower side.

Leaflets:
*Shape.*—Oval.
*Texture.*—Leathery. Under side smooth. Ribs and veins ordinary.

*Edge.*—Serrated.
*Serration.*—Single, small sized.
*Petiole.*—(*rachis*).—Color—green. Underside—few prickles.
*Stipules.*—Short and smooth.
*Disease Resistance.*—Resistant to mildew under normal growing conditions at Irvine, Calif.

Wood:
*New wood.*—Color—light green. Bark—smooth.
*Old wood.*—Color—green. Bark—smooth.

Prickles:
*Quantity.*—On main stalks—ordinary. On laterals—ordinary.
*Form.*—Broad based, hooked downward.
*Color.*—When young—red.
*Position*—Irregular.

Small Prickles:
*Quantity.*—On main stalks—many. On laterals—few.
*Color.*—Red when young.

I claim:

1. A new and distinct variety of rose plant of a class between hybrid tea and floribunda, substantially as herein shown and described, characterized particularly as to novelty by the unique combination of its floribunda type plant but of a general large size; its hybrid tea type and size blooms; its Signal red bud and Mandarin red bloom; its long keeping qualities as a cut flower and its relatively strong resistance to rose powdery mildew.

No references cited.

ROBERT E. BAGWILL, Primary Examiner

PO-1050
(5/69)

UNITED STATES PATENT OFFICE
CERTIFICATE OF CORRECTION

Patent No. Plant 3510 Dated March 5, 1974

Inventor(s) WILLIAM A. WARRINER

It is certified that error appears in the above-identified patent and that said Letters Patent are hereby corrected as shown below:

Column 1, line 19, "of" should read --and--.
Column 2, line 66, "(0961/1)" should read --(0960/1)--.

Signed and sealed this 17th day of September 1974.

(SEAL)
Attest:

McCOY M. GIBSON JR.
Attesting Officer

C. MARSHALL DANN
Commissioner of Patents